United States Patent [19]

Avery

[11] Patent Number: 4,794,657

[45] Date of Patent: Jan. 3, 1989

[54] TUMMY HUGGER PILLOW COMBINATION

[76] Inventor: Linda S. Avery, 8802 Chambers Pl., N.E., Albuquerque, N. Mex. 87111

[21] Appl. No.: 66,353

[22] Filed: Jun. 25, 1987

[51] Int. Cl.⁴ .................... A47C 20/00; A47C 20/02
[52] U.S. Cl. .......................................... 5/431; 5/437; 5/436; 5/465
[58] Field of Search ................ 5/431, 434, 436, 437, 5/441, 442, 465

[56] References Cited

U.S. PATENT DOCUMENTS

| | | | |
|---|---|---|---|
| 2,167,178 | 7/1939 | Kohlstadt | 5/436 X |
| 4,242,767 | 1/1981 | McMullen | 5/465 |
| 4,394,783 | 7/1983 | Simmons | 5/437 X |
| 4,459,714 | 7/1984 | Lin | 5/465 X |
| 4,624,021 | 11/1986 | Hofstetter | 5/436 X |

Primary Examiner—Michael F. Trettel
Attorney, Agent, or Firm—James E. Snead

[57] ABSTRACT

A pillow assembly has parts thereof made into a trunk, head, and leg pillows, all adapted to be attached together in a particular manner to enable the trunk pillow to be hugged against one's stomach, the leg pillow to be squeezed between one's legs, and a head pillow to receive one's head. A lower end of the head pillow may be removably received by the upper end of the trunk pillow. An upper end of the leg pillow may be removably received by the lower end of the trunk pillow. The pillows are arranged along a common longitudinal axis. The leg and head pillows can be axially and longitudinally positioned respective to one another and to the trunk pillow into an infinite number of different positions and lengths.

4 Claims, 1 Drawing Sheet

U.S. Patent
Jan. 3, 1989
4,794,657
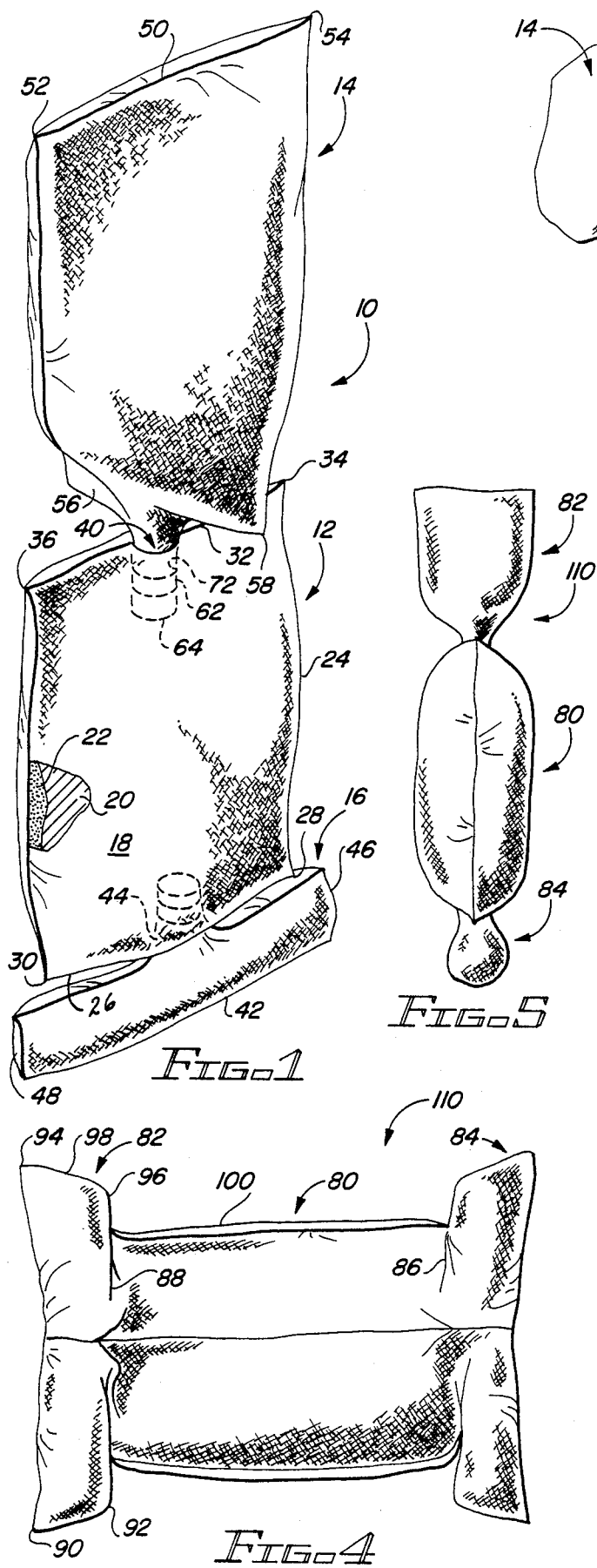
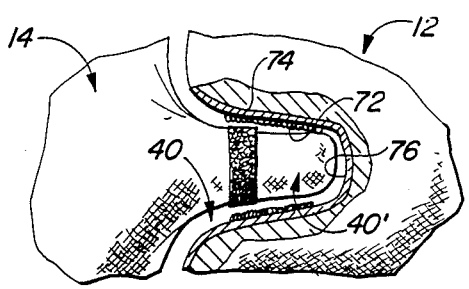
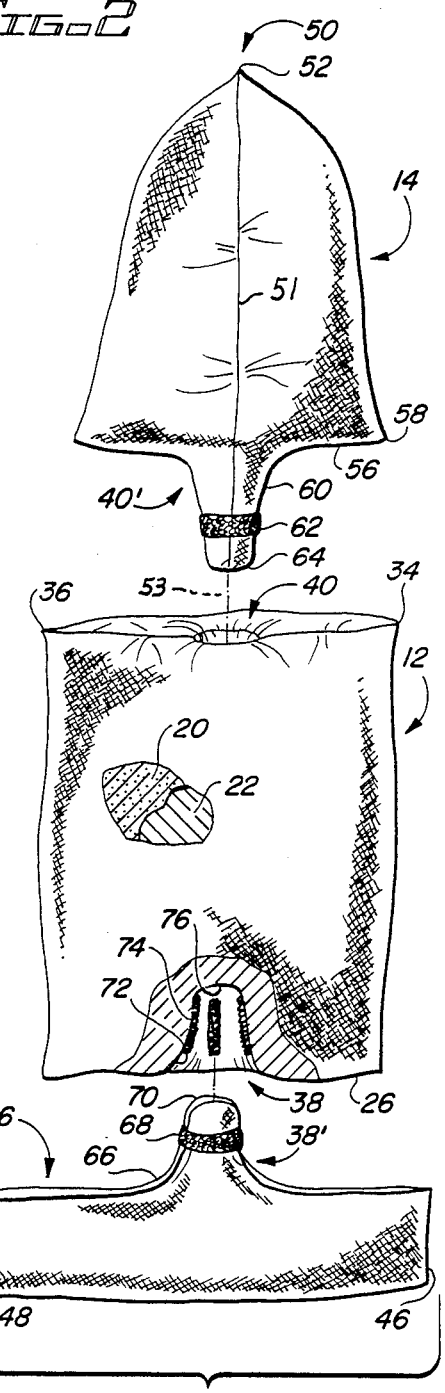

TUMMY HUGGER PILLOW COMBINATION

BACKGROUND OF THE INVENTION

Many people have a need to support their stomach after surgery or to separate body members such as legs, after surgery or child delivery, and in some people there is an inherent compulsion to assume the fetal position when relaxed, lying in bed, awaiting sleep. Some people assume this position as a matter of natural relaxation and often find it satisfying to hug a pillow against their stomach, thereby augmenting the restful condition they have assumed. Additionally, other types of surgery make it desirable as a matter of comfort to hug a pillow against the stomach, or between the legs or both, while resting the head on part of the pillow. However, there is until the time of this invention no single pillow made into a configuration which enables the simultaneous use of a pillow placed at these strategic parts of the anatomy.

Accordingly, the present invention provides a unique pillow which can be advantageously used wherein the head, stomach, and legs separately, simultaneously or in a variety of combinations come to bear against portions of the new pillow in a manner that increases the comfort or is pleasing and satisfying to the user. A special pillow which enables all of the above desirable attributes to be realized in a variety of combinations is the subject of this invention.

RELATED ART

Lynch U.S. Pat. No. 3,604,023 recognizes that body support at various locations is important.

Jacobson U.S. Pat. No. Des. 201,492 and Rinz U.S. Pat. No. Des. 258,793 show pillow constructions having more than one part which could be used for resting more than just one's head, as suggested in Gonzalez-Rincones U.S. Pat. No. 3,149,140 and in Tobias U.S. Pat. No. 2,577,595.

McCullough U.S. Pat. No. 3,327,330 and Varaney U.S. Pat. No. 4,173,048 show a pillow made in multiple parts.

SUMMARY OF THE INVENTION

A pillow assembly can be simultaneously received between one's legs, against one's stomach, and under one's head or in a variety of combinations. The pillow assembly comprises the combination of a trunk pillow, a head pillow, and a leg pillow, all of which may be attached together or in a variety of combinations.

The head pillow has a first and a second end with the second end being adapted to be removably attached to the first end of the trunk pillow. The leg pillow has a first and a second end with the first end thereof being adapted to be removably attached to the second end of the trunk pillow. The trunk pillow has first and second ends, respectively, adapted to be removably attached to the near ends of the head and leg pillows, respectively.

The head pillow and leg pillow are adapted to be removably attached to the trunk pillow by a female and a male socket mechanism. Preferably a female socket is formed in opposed ends of the trunk pillow and the surface of the female socket is supplied with a suitable fastening means, such as Velcro fastening material or the like. The head and leg pillows each have a terminal end which is made into a male socket. The male socket has suitable fastening means, such as Velcro fastening material or the like thereon, and is received within the female socket. This unusual construction enables the head and leg pillows to be removably attached to the opposed ends of the trunk pillow. Furthermore, either the head or leg pillows can be axially positioned with respect to one another and to the trunk pillow. This enables the pillow assembly to be put together in a variety of configurations and the members to be positioned in an infinite number of different configurations.

Accordingly, a primary object of the present invention is the provision of a pillow assembly which can be put together in a variety of configurations and which can, if desired, be assembled to be simultaneously received between one's legs, against the stomach, and under one's head.

Another object of the present invention is the provision of a pillow assembly having a trunk pillow to which there may be removably attached a head pillow and a leg pillow, each of which can be axially positioned respective to the other.

A further object of this invention is the provision of a pillow assembly having a main trunk pillow to which there may be removably attached a head pillow and a leg pillow at opposed ends thereof.

These and various other objects and advantages of the invention will become readily apparent to those skilled in the art upon reading the following detailed description and claims and by referring to the accompanying drawings.

The above objects are attained in accordance with the present invention by the provision of a combination of elements which are fabricated in a manner substantially as described herein.

BRIEF DESCRIPTION OF THE DRAWINGS

FIG. 1 is a perspective view of a pillow assembly made in accordance with the present invention, with some interior parts being shown in outline or partial cut-away form to disclose the interior thereof;

FIG. 2 is an enlarged, fragmentary, part cross-sectional view which sets forth some additional details of part of the pillow assembly disclosed in FIG. 1;

FIG. 3 is a disassembled view of the pillow assembly disclosed in FIG. 1, with some cut-away views being shown in order to more fully disclose the invention;

FIG. 4 is a top, plan view of another embodiment of the pillow assembly made in accordance with the present invention; and, FIG. 5 is a side view of the pillow assembly disclosed in the foregoing figures.

DETAILED DESCRIPTION OF THE PREFERRED EMBODIMENTS

In the figures of the drawings, and in particular FIGS. 1-3, there is disclosed a pillow assembly 10 made in accordance with the present invention. The pillow assembly 10 includes the combination of a trunk pillow 12, a head pillow 14, and a leg pillow 16 removably attached together in a manner which will be more fully described hereinafter. As seen in FIG. 1, the trunk pillow 12 has an outer surface or cover 18 which can be any type of cloth or woven material, and which encapsulates pillow material 22 therein. An inner cover 20 can be provided if desired. The pillow material 22 can be any acceptable light weight material for suitably filling pillows including sponge rubber, feathers, and other pillow filler material known to those skilled in the art of fabricating pillows.

The trunk pillow 12 has the illustrated longitudinally extending opposed sides 24 which terminate at the bottom 26 thereof to form the illustrated opposed corners 28 and 30 at the bottom of the trunk pillow 12.

The top 32 of the trunk pillow 12 extends laterally in a manner similar to bottom 26 and intersects the opposed longitudinal extending sides 24 at the illustrated corners 34 and 36.

As best seen illustrated in FIG. 3, together with other figures of the drawings, the trunk pillow includes a lower female socket 38 that releasably engages a male complementary made socket 38' formed on the leg pillow 16. An upper female socket 40 removably receives a complementary made male socket 40' formed on the head pillow 14. The male and female sockets 38, 38' and 40, 40' are releasably engageable respective to one another in a manner which will be more fully explained hereinafter. The sockets 38, 38' and 40, 40' lie along a common longitudinally extending axial centerline 53 and thereby enable the head pillow 14 to be axially rotated into any one of an infinite number of different positions; and, the lower leg pillow 16 to be axially rotated into any one of an infinite number of different positions respective to the trunk and head pillows.

In FIGS. 1 and 3, the leg pillow 16 has a lower opposed end 42 that forms the lowermost part of the pillow assembly. The leg pillow has a side 44 shown in FIG. 1 which necks down at 66 to form the before mentioned male socket 38'. The leg pillow extends laterally respective to the trunk pillow and terminates at sides 46 and 48.

The head pillow 14 includes an upper terminal end 50 that extends laterally of the longitudinal axis of the pillow assembly and terminates at corners 52 and 54. The corners 52 and 54 define the upper extremity of the opposed longitudinally extending sides of the head pillow. The opposed sides extend downward from corners 52 and 54, and form corners 56 and 58. The lower end of the head pillow 14 curves at 60 into joined relationship respective to the make socket member 40' as is more particularly shown in FIG. 3. Hook and loop fastener means, such as the well known Velcro TM fastener, or the like, 62 is applied on a medial length to the exterior surface of the male socket 40'. The male socket 40' terminates at end part 64.

Numeral 66 indicates the neck of the male socket 38' on the leg pillow 16. The hook and loop fastener material, or the like, 68 is placed on a medial length of the socket 38'. The socket 38' terminates at upper end portion 70.

Female socket 38 in trunk pillow 12 includes a male socket receiving part 72 made complementary respective to part 66, and includes hook and loop fastener material, or the like, 74 formed thereon, An innermost back wall 76 abuttingly receives the end 70 of the male socket part 38' if it is fully inserted into female socket 38. The bottom wall 76 of the opposed ends of the female sockets 38 and 40 preferably are tied together internally or otherwise affixed within the pillow as by a length of stout cord so that they will not be pulled out when the head and leg pillows are removed.

In FIGS. 2 and 3, it is shown that fastener material can be applied as a ring to the outer wall of each male socket member, and as a plurality of radial strips to the inner wall of the female socket member. This also allows for flexibility in determining length of extension of pillow parts. The extent to which it is inserted into the female socket member will add or subtract several inches total length of the entire pillow. The male socket may be pulled out to the end of the strips of hook and loop fastener material on the outside edge of the female socket without exposing the user to the rough component fastener material.

FIGS. 4 and 5 set forth an alternate embodiment 110 of the present invention. As particularly seen disclosed in FIG. 4, there is a trunk pillow 80 to which there is attached in a more or less permanent manner opposed head and leg receiving pillow parts 82 and 84. Opposed pillow parts 82 and 84 may be identical. The pillow 110 is symmetrical about the axial centerline thereof.

Numerals 86 and 88 in FIG. 4 indicate the attachment area where the head and leg receiving pillow parts 82 and 84 are attached to trunk pillow 80. Pillow part 82 terminates at corners 90, 92, 94, and 96.

The pillow part 82 has laterally extending opposed sides which terminate at 98. Numeral 100 indicates a side of the trunk pillow 80.

I claim:

1. A pillow assembly comprising a head pillow, a trunk pillow and a leg pillow; attachment means by which the head pillow, trunk pillow, and leg pillow are connected together in series relationship whereby the pillow assembly may be simultaneously received under a user's head, against the stomach and between the legs;

said head pillow having a first end attached to said trunk pillow; and a second end which forms an upper terminal end of the pillow assembly;

said leg pillow having a first end attached to said trunk pillow and a second end which forms a lower terminal end of the pillow assembly;

said trunk pillow having one end which is attached to the first end of said head pillow and a second end which is attached to the first end of said leg pillow;

each said attachment means includes a single axially symmetrical male and female socket member having fastener material formed thereon which enables the male socket member to be removably connected within said female socket member;

said head and leg pillows each have one of said male and female socket members formed thereon, and said trunk pillow has the other of said male and female socket members formed thereon.

2. The pillow assembly of claim 1 wherein said fastener material of said attachment means is hook and loop type fastener material.

3. A pillow assembly comprising a trunk pillow, a head pillow, and a leg pillow, attachment means by which the trunk, head, and leg pillows are all removably attached to one another in a manner to enable the pillow assembly to be simultaneously received between the legs, against the stomach, and under one's head;

said head pillow having a first end opposed to a second end with said second end being removably attached to said trunk pillow by said attachment means; and, said first end forming the terminal end of the pillow assembly;

said leg pillow having a first end opposed to a second end with said second end being removably attached to said trunk pillow by said attachment means and said first end forming the lower terminal end of the pillow assembly;

said trunk pillow having first and second ends, respectively, attached to the second ends, respectively, of said head and leg pillows;

each said attachment means includes a single axially symmetrical male and female socket member having fastener material formed thereon which enables the male socket member to be removably connected within said female socket member;

said head and leg pillows each have one of said male and female socket members formed thereon, and said trunk pillow has the other of said male and female socket members formed thereon.

4. The pillow assembly of claim 3 wherein said fastener material of said attachment means is hook and loop type fastener material.

* * * * *